(12) United States Patent
Bjarnason et al.

(10) Patent No.: US 7,070,953 B1
(45) Date of Patent: Jul. 4, 2006

(54) PROTEIN HYDROLYSATES PRODUCED WITH THE USE OF COD PROTEASES

(75) Inventors: Jon Bragi Bjarnason, Reykjavik (IS); Bergur Benediktsson, Reykjavik (IS)

(73) Assignee: Nordur EHF, Reykjavik (IS)

( * ) Notice: Subject to any disclaimer, the term of this patent is extended or adjusted under 35 U.S.C. 154(b) by 323 days.

(21) Appl. No.: 10/110,977

(22) PCT Filed: Oct. 20, 2000

(86) PCT No.: PCT/IS00/00012

§ 371 (c)(1), (2), (4) Date: Jun. 18, 2002

(87) PCT Pub. No.: WO01/28353

PCT Pub. Date: Apr. 26, 2001

(30) Foreign Application Priority Data

Oct. 20, 1999 (IS) .......................................... 5225

(51) Int. Cl.
C12P 21/06 (2006.01)

(52) U.S. Cl. ..................... 435/68.1; 435/226; 435/183; 435/195; 435/198; 426/63

(58) Field of Classification Search ............... 435/68.1, 435/183, 195, 198, 226, 201, 209, 212, 213, 435/218, 219
See application file for complete search history.

(56) References Cited

U.S. PATENT DOCUMENTS 3,836,686 A * 9/1974 Roels .......................... 426/657

| | | |
|---|---|---|
| 3,852,479 A | 12/1974 | Yokotsuka et al. |
| 5,532,007 A | 7/1996 | Pedersen et al. |
| 5,866,357 A | 2/1999 | Dambmann et al. |
| 5,945,102 A | 8/1999 | de Faire et al. |

FOREIGN PATENT DOCUMENTS

| | | |
|---|---|---|
| CA | 1313835 | 2/1993 |
| EP | 0797928 A1 | 10/1997 |
| EP | 0823998 A2 | 2/1998 |
| FR | 2352498 | 5/1976 |
| WO | 89/10960 | 11/1989 |
| WO | 94/25580 | 11/1994 |
| WO | 98/27827 | 7/1998 |

OTHER PUBLICATIONS

University of Guelph, "Yogurt" accessed Oct. 21, 2004 http://www.foodsci.uoguelph.ca/dairyeu/yogurt.html.*

(Continued)

*Primary Examiner*—Leon B. Lankford, Jr.
*Assistant Examiner*—Allison M. Ford
(74) *Attorney, Agent, or Firm*—Hunton & Williams (57) ABSTRACT

The invention relates to a method for enzymatically obtaining protein hydrolysates for human consumption, animal feed and cosmetics. The process involves the use of a proteolytic composition derived from fish, such as Cod (*Gadus morhua*), to obtain hydrolysates which have a non-bitter taste and retain the flavor and aroma of the protein-containing material which is hydrolyzed: e.g. when hydrolyzing protein-containing material from marine organisms or parts thereof, such as fish, shrimp, lobster or other seafood according to the invention, a protein hydrolysate is produced that has a characteristic natural flavor of the organism Also provided are food products comprising the hydrolysates of the invention, such as soup, sauce, cheese, HVP, meat extract and flavoring agent, broth, paté, mousse, frying dough, orly dough, and pastries.

41 Claims, 3 Drawing Sheets

OTHER PUBLICATIONS

Worthington Catalog, http://www.worthington-biochem.com, "Amylase, Alpha" "Cellulase" "Pectinase" accessed Oct. 21, 2004.*

Kikkoman, "Glutaminase (GLN)", www.kikkoman.co.jp/bio/j/rinsyou/pdf/28_GLN.pdf accessed Oct. 21, 2004.*

Huachang Group "Jiangsu Huachang, B-Glucanase" http://huachang.en.alibaba.com/product/50007034/50044361/Enzymes/_beta_Glucanase.htm☐☐accessed Oct. 21, 2004.*

Magnus M. Kristjansson et al., "Characterization of a collagenolytic serine proteinase from the Altantic cod (*Gadus morhua*)", Comp. Biochem. Physiol., vol. 110B, No. 110B, No. 4, pp. 707-717, 1995.

Bjarni Asgeirsson, et al., "Purification and characterization of trypsin from the poikilotherm *Gadus morhua*", Eur. J. Biochem, vol. 180, pp. 85-94, 1989.

Bjarni Asgeirsson, et al., "Structural and kinetic properties of chymotrypsin from Atlantic cod (*Gadus Morhua*). Comparison with bovine chymotrypsin", Comp. Biochem. Physiol, vol. 99B, No. 2, pp. 327-335, 1991.

Bjarni Asgeirsson, et al., "Properties of elastase from Atlantic cod, a cold-adapted proteinase", Biochemica et Biophysica Acta, vol. 1164, pp. 91-100, 1993.

Database WPI, Section Ch, Week 199649, Derwent Publications Ltd., London, GB; AN 1996-495762XP002901515 & RU 2 055 482 C (As USSR far E Pacific Bioorg Chem Inst.), Mar. 10, 1996, ABSTRACT (English language).

* cited by examiner

PROTEIN HYDROLYSATES PRODUCED WITH THE USE OF COD PROTEASES

CROSS-REFERENCE TO RELATED APPLICATIONS

This is a U.S. national stage under 37 U.S.C. § 371 of International Application PCT/IS00/00012, filed Oct. 20, 2000, which claimed priority from Iceland application 5225 filed Oct. 20, 1999.

TECHNICAL FIELD

The present invention relates to a method of hydrolyzing proteins, protein hydrolysates obtained by the method, and food products and non-food products comprising the hydrolysates of the invention.

BACKGROUND AND PRIOR ART

Methods of hydrolyzing proteins are well known in the art. Conventionally, protein hydrolysates are produced chemically by hydrolyzing protein or proteinaceous material, such as for example defatted soy flour or wheat gluten, with hydrochloric acid under refluxing conditions. The resulting hydrolysates are inexpensive and can have satisfactory organoleptic properties. However, chemical hydrolysis is accompanied by non-specific side reactions causing e.g. the formation of chlorohydrins, such as monochlorodihydroxypropanols (MCDPs) and dichloropropanols (DCPs), the presence of which is undesirable in food products. The food industry is demanding milder methods of modifying food products, reducing the need for harsh, chemical reaction conditions and for removal of side-reaction products and residual reagents.

Alternatively, protein or proteinaceous material may be hydrolyzed enzymatically. Typically, the relevant protein source is first subjected to a (partial) hydrolysis with one or more suitable endoproteases. Then, the resulting protein fragments can be degraded completely or partially into individual amino acids or dipeptides or tripeptides by the use of exopeptidases. Alternatively, the endopeptidases and exopeptidases may function simultaneously in an enzyme mixture resulting in a similar complete or partial degradation of the protein or proteinaceous material.

A fundamental problem in the enzymatic hydrolysis of proteins and proteinaceous material is the formation of a bitter flavor due to the formation of short peptide fragments. The bitter taste is believed to be the result of cleavage of proteins at amino acids with hydrophobic side chains, resulting in the formation of peptides with exposed hydrophobic side chains, which are typically inaccessible in proteins and longer peptides due to their tertiary structure.

In order to solve this problem, the state of the art proposes to use specific proteases to limit the degree of hydrolysis and obtain preferred terminal side-chains. For example, U.S. Pat. No. 5,866,357 describes the use of a Glu/Asp specific protease for the preparation of hydrolysates, optionally with the use of an additional specific protease. Furthermore, WO 98/27827, for example, proposes, for the purpose of solving the problem, using a proteolytic enzyme mixture comprising only one exopeptidase, wherein the exopeptidase is produced using rDNA techniques, and may be employed in combination with one or more suitable endopeptidases, such as Fromase™ (Gist-Brocades, France) and Maxatase™ (Genencor International, Belgium). U.S. Pat. No. 5,532,007 discloses the use of a combination of purified enzymes, a neutral protease producible by means of a *Bacillus* strain and an alkaline protease producible by means of a *Bacillus* strain. The reference states that raw meat is preferably treated with proteases exclusively with endo-activities for the purpose of the described invention to obtain meat hydrolysates. Methods disclosed in WO 94/25580 employ a proteolytic enzyme preparation derived from the fungus *Aspergillus oryzae* (Flavorzyme™) comprising a mixture of endopeptidases and exopeptidases.

Alternatively, EP 0 823 998 A2, proposes the enzymatic hydrolysis of smoked meat as the protein or proteinaceous material for the generation of a protein hydrolysate which does not taste bitter. In this process it is preferred that only one enzyme, preferably a neutral or an alkaline protease having an endopeptidase effect, for example Pescalase (Gist Brocades), Alcalase (Novo Nordisk) or Promod 31 (Biocatalysts), be employed for the hydrolysis.

WO 89/10960 proposes the use of complex enzyme mixtures from krill to modificate protein, peptide and/or lipid constituents of biological material in industrial processes. The enzyme compositions disclosed are prepared by incubating macerated whole Antarctic krill (*Euphasia superba*) at 50° C. for 20 h. Examples of various applications are described, such as hydrolysis of fish and meat. The krill enzyme preparations are said to contain different proteases and lipolytic enzymes, e.g. a considerable amount of phospholipases. Such preparations do not seem to have been used on a commercial scale for the production of food-grade hydrolysates. It should be noted that in all of these prior art references, hydrolysates are obtained by enzymatic incubation at 50–65° C.

WPI abstract AN 1996495762 (RU-C-2 055 482) describes the use of pylloritic enzymes from Salmon for the production of protein-nucleic hydrolysates, but low-temperature hydrolysis is not discosed or anticipated. U.S. Pat. No. 3,852,479 describes a process for producing protein hydrolysates having a high glutamic acid content, by hydrolyzing protein material with a glutaminase together with a proteolytic enzyme. Also herein are temperature above 50° C. preferred. CA 131385 describes the use of porcine trypsin or Enzeco AP-1™ protease (alkaline phosphatase of bacterial origin) for enzymatic extraxtion of carotenoprotein from crustacean wastes. None of these references disclose the use of proteases from Gadiform fish species for producing protein hydrolysates or suggest that such or other similar enzyme compositions would be effective at low temperatures.

For the production of many delicate processed food products originating from or simulating natural products, such as, e.g. seafood soups and sauces, flavor extracts need not only have non-bitter properties but must also exhibit the same or a very similar flavor as the characterizing flavor of the natural product. Most quality-restaurants still prepare extracts for e.g. shellfish soups using conventional methods of making a stock from shells, claws, heads etc. Enzymatically prepared flavor agents have generally not been used widely as they do not seem to provide a satisfactory natural flavor.

The odors of fish and other seafood species are produced by complex mixtures of volatile compounds, and are very sensitive to conditions affecting the freshness of the species. Species-related odor compounds in fresh fish are present in very low levels, but many of such compounds have low odor thresholds and therefore, even though present in low levels (ppb) they still affect the overall aroma of the fish species and changes in their concentrations drastically affect the overall aroma. These compounds include unsaturated carbonyl compounds and alcohols with six, eight, or nine carbon atoms. Also, bromophenols in low concentrations have been associated with the natural, sea-, iodine, marine-like flavors of seafood. Microbial compounds are microbially formed during spoilage of fish. These include short chain alcohols, ketones, aldehydes, amines, sulphur compounds, aromatics and acids, and result mainly from the degradation of amino- and fatty acids. Proteolytic activity will accelerate the spoilage as small peptides and free amino acids are nutrients for bacteria, resulting in the formation of bad smelling metabolites. Therefore, careful selection of conditions for the hydrolysis of seafood and related protein materials is highly critical for the production of such hydrolysates for high-quality food products with desirable organoleptic properties. It is likely that prolonged incubations at temperatures in the range of 50–65° C. will degrade the overall flavor and aromatic character of the protein-containing materials being hydrolyzed, in particular of fish and other seafood material, due to the loss of volatile compounds and production of undesired side-reaction products.

There is a need for methods of hydrolyzing proteins under mild conditions leading to high yields and to hydrolysates with excellent organoleptic properties, in particular protein hydrolysates that have preserved the natural flavor of the protein-containing starting material such as seafood, but which do not have the bitter flavor which arises during conventional hydrolysis of protein-containing materials. It has been found that methods for obtaining hydrolysates at low enzyme incubation temperatures result in that the freshness and flavor (volatile flavor agents) of the raw material can be preserved, assumingly due to a reduced level of side-reactions and microbial activity and that a relatively non-specific enzyme preparation derived from fish intestines and obtainable with economical and technically simple methods can be used for effective hydrolysis of proteinaceous materials to obtain hydrolysates that are non-bitter and retain excellent flavor characteristics of the protein-containing raw material. A particularly advantageous aspect of the invention is the low temperature range at which such enzyme preparations are proteolytically active. It is conceivable that the low temperature range at which the methods and processes of the invention are preferably carried out at is an important factor contributing to the organoleptic properties of the obtained products.

SUMMARY OF THE INVENTION

Accordingly, in a first aspect, the invention provides a method for producing a protein hydrolysate from a natural protein-containing raw material, the method comprising the steps of: a) preparing an aqueous slurry comprising 1–100% wt of protein-containing material; b) incubating the slurry with a proteolytic composition derived from fish; c) agitating the slurry for 0.25 to 48 hours at a temperature in the range of about 0 to about 60° C.; d) optionally inactivating the proteolytic mixture; and e) optionally separating the solution fraction from solid material.

In a further aspect, a protein hydrolysate is provided which is obtained by the method of the invention.

In yet a further aspect, the invention further provides a food product comprising a protein hydrolysate obtained according to the invention.

The invention provides in a still further aspect, a process for preparing a food product comprising the steps of obtaining a protein hydrolysate according to the invention and formulating a food product using the hydrolysate.

In another aspect of the invention, a process is provided for producing a flavor preparation, the process comprising the steps of a) preparing an aqueous slurry comprising 1–100% wt protein-containing material; b) incubating the slurry with a proteolytic composition derived from fish; c) agitating the slurry for 0,25 to 48 hours at a temperature in the range of about 2 to about 40° C.; d) optionally inactivating the proteolytic mixture; e) separating the solution fraction from solid material; and f) concentrating the solution to a dry weight content of from about 10 wt % to about 98 wt %.

In still a further aspect of the invention, a non-food product is provided comprising a protein hydrolysate according to the invention.

In yet another aspect, the invention provides a method for releasing at least part of the astaxanthin from an astaxanthin-containing shellfish material, the method comprising the steps of preparing as the starting material an aqueous slurry comprising the shellfish material; incubating the slurry with a proteolytic composition derived from fish, agitating the slurry at a temperature in the range of about 2 to 60° C.; and inactivating the proteolytic mixture to obtain a protein hydrolysate containing, relative to the starting material, a higher content of released astaxanthin.

DETAILED DESCRIPTION OF THE INVENTION

The proteolytic compositions used according to the invention are derived from the intestines of cold water fish, thus rendering them unusual characteristics such as, in particular, a high activity at low temperatures. The detailed characterization of a proteolytic preparation from Cod (*Gadus Morhua*) intestines has shown that the preparation comprises several proteolytic components. It has been observed that the preparation comprises at least five or more proteolytic enzyme components or groups. These proteolytic components or groups comprise the endopeptidases trypsin, at least three isozymes (Ásgeirsson et al., 1989), chymotrypsin, at least two isozymes (Ásgeirsson and Bjarnason, 1991), and elastase, at least one isozyme (Ásgeirson and Bjarnason, 1993), and the exopeptidases of the aminopeptidase and carboxypeptidase types.

It has been found that such preparations not only serve as a useful source of the above individual enzyme components, but also surprisingly that they can be efficiently used for producing protein hydrolysates with unusual characteristics, i.e. which are non-bitter and retain the flavor characteristics of the protein-containing raw material.

As mentioned, the invention provides a method for producing a protein hydrolysate from a natural protein-containing raw material. The method comprises as a first step the preparation of an aqueous slurry comprising about 1 to 100 wt % of protein-containing material, preferably about 10–100 wt %, such as e.g. in the range of about 25–100 wt %. The material may be pre-treated with conventional means such as mechanical shredding, cutting, mincing, or grinding. The content of protein-containing material in the slurry will depend on the water content and texture of the material, e.g. when hydrolyzing flesh of white fish with a dry weight content of about 18–25%, additional water may not be needed. However, for hydrolyzing material with a higher dry weight content, water is added to the slurry to obtain a dry weight content of the slurry of about 1–30%, preferably about 5–25%, such as about 10–20%.

The slurry is thereafter incubated with a proteolytic preparation derived from fish, and the slurry is agitated for 0.25 to 48 hours, preferably about 1 to 10 hours, more preferably about 1 to 6 hours, including 2 to 4 hours. The incubation is performed at any convenient temperature at which the enzyme composition does not become heat inactivated, i.e. in the range of from about 0° C. to about 60, but preferably from about 2 to about 40° C., including about 5 to 35° C., and more preferably in the range of about 5 to 30° C., such as about 10 to 25° C., including about 15° C., about 17° C., and about 20° C. In certain embodiments, a particularly low temperature range may be desirable, such as e.g. about 2–10° C., including about 2–8° C. Generally, lower incubation temperatures are compensated with longer incubation times or a higher relative concentration of the proteolytic composition, or both. Low incubation temperatures, such as temperatures below about 40° C., particularly below about 25–30° C. are conceivably an important factor contributing to the retention of the flavor and aroma of fresh, delicate protein-containing materials to be used for food-grade hydrolysates, as discussed above.

Figure 2:
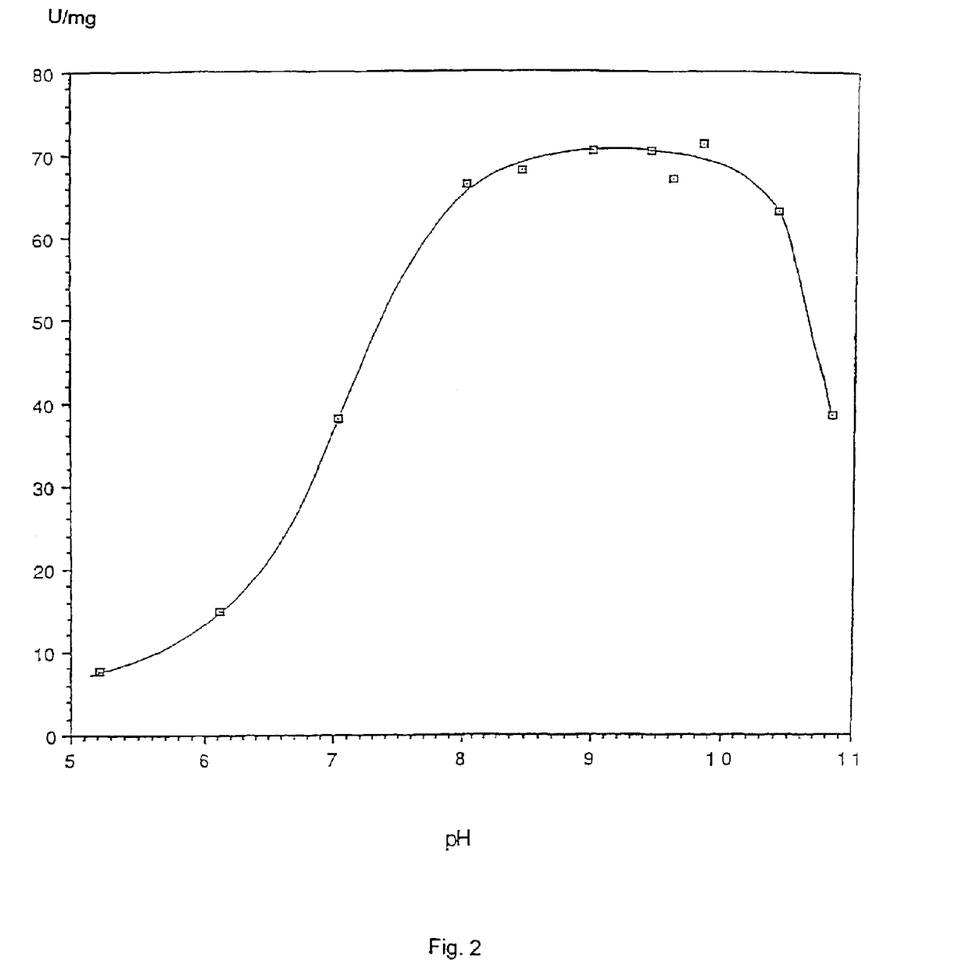
Figure 3:
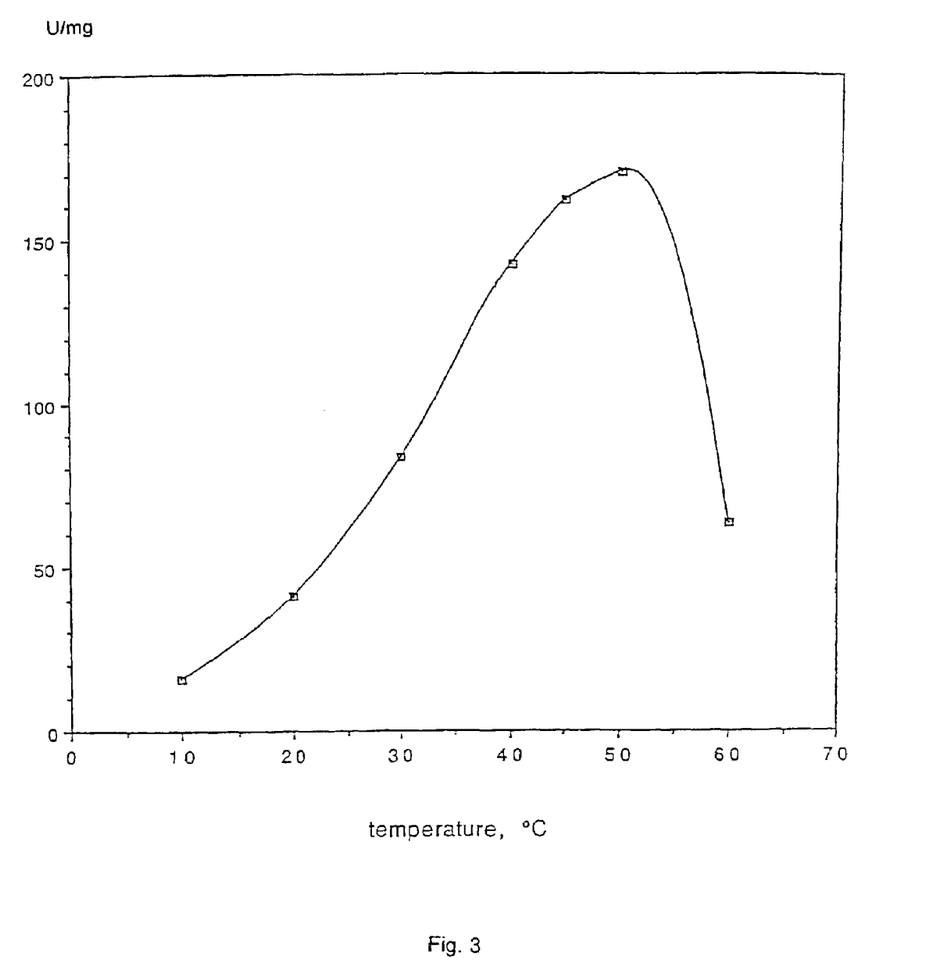

In accordance with established practice, the proteases in the incubation mixture may optionally be suitably inactivated, such as e.g. by quick heating to above about 60° C., such as to about 70° C., or by decreasing the pH of the incubation mixture to a pH at which the proteases become inactivated, such as to below about pH 5, as can be seen in FIG. 2 and FIG. 3 for a proteolytic preparation derived from Cod.

The solution fraction, containing dissolved, hydrolyzed peptides is then optionally separated from solid material, e.g. by sedimentation, filtration, or centrifugation. The enzyme inactivation may optionally be performed after such separation, on the solution fraction alone or both fractions separately.

For certain protein-containing materials, it is advantageous to heat the material prior to the step of hydrolysis, to minimize eventual microbial contamination, and/or to inactivate other enzymes causing undesired reactions. The inventors have found that e.g. when hydrolyzing lobster flesh, quick heating to a temperature of about 70–90° C. eliminates the activity of phenyloxidases that otherwise will darken the lobster flesh and the resulting hydrolysate.

As a further optional step, the solution fraction may be concentrated to a desired dry matter content by any applicable means such as evaporative heating under vacuum or lyophilization. The dry matter content of the hydrolysate product is anywhere in the range of about 1 to 100%, depending on the desired form and liquid content of the product, liquid or semi-liquid hydrolysate preparations will typically have a dry matter content of about 5–40%, including about 15–35%. The hydrolysate product may alternatively be in the form of a gel or a paste, or in a solid or semi-solid form such as e.g. flakes, a powder form, or as compressed bodies, e.g. as tablets, bars, cubes, or blocks.

The incubation is performed at a pH in the range of about 6 to about 11, preferably between about 7 to 10. As demonstrated with a Cod-derived proteolytic composition in FIG. 1 and FIG. 2, the method of the invention performs reasonably well even at the rather extreme conditions, i.e. at pH values in the full range of 6 to 11.

The proteolytic composition is in useful embodiments derived from *Gadiform* species, including *Gadidae* (cod species and hakes) and grenadiers. Atlantic Cod (*Gadus morhua*) is a readily available and particularly useful source of the composition. Other fish species which are used as a source of the proteolytic composition in further embodiments include haddock, pollack (saithe), salmon, trout, perch, mackerel, sardine, herring, and capelin. Preferred species include in particular those from which the intestines can readily be separated from other viceral organs.

In a particularly useful embodiment, the proteolytic composition is provided by a process comprising the steps of mixing water with fish viscera; agitating the mixture for a period of 0.5 hours or longer, such as in the range of about 1–10 hours, and preferably about 2–6 hours; separating solid residue from the solution, e.g. by sedimentation, filtration, or centrifugation; and concentrating the aqueous solution to obtain the proteolytic composition. Fish viscera in this context comprise fish intestines, e.g. the pyloric caeca, however, in a preferred embodiment, the liver, milt, roe and the stomach are removed from the viscera prior to the preparation. The inventors have observed that most of the preferred active proteases are derived from the less acidic intestines and not the more acidic stomach. The concentration step is performed with any suitable means well known to the person skilled in the art, such as, e.g. ultrafiltration, to obtain a desired activity per volume unit, such as, e.g. in the range of about 0.1–100 BAPNA units/mL measured as described in Example 1, more preferably in a range of about 0.5–10 BAPNA U/mL, including about 1–5 BAPNA U/mL.

The agitation of the water-viscera mixture is performed at a pH and temperature at which the stability of the desired proteases is not decreased substantially from their optimum, such as e.g. at a temperature in the range of about 0–20° C., and at a pH in the range of 6–11. In a preferred embodiment, the agitation of the water-viscera mixture is performed at a pH in the range of about 6 to about 9, including a range of about 6 to 8, such as e.g. about 6 to 8, and preferably at a temperature in the range of about 0 to about 15° C., including about 0–10° C., more preferably about 0–5° C.

The proteolytic composition comprises in one embodiment of the invention, at least one enzyme selected from the group consisting of trypsin, chymotrypsin, elastase, collagenase, aminopeptidase, and a carboxypeptidase type enzyme. Preferably, the composition comprises two or more of the above-mentioned enzymes, such as e.g. all of the enzymes. However, in certain useful embodiments, the proteolytic composition is further refined by the removal of at least one of its enzyme components. Example 2 demonstrates how elastase and serine collagenases are removed from a proteolytic composition derived from Cod to obtain a modified Cod-derived enzyme composition with many of the same characteristics as the basic composition of Example 1.

The proteolytic composition used according to the invention, preferably has an enzymatic activity in the range of about 0,1 to about 100 BAPNA units/mL, measured as in the assay of Example 1 herein, more preferably about 0.5 to about 20 BAPNA units/mL, even more preferred about 1–10 units/mL, including about 1 to 5 units/mL. The suitable amount of enzyme composition to incubate the protein material slurry with will depend on the specific activity of the enzyme composition, the desired time-range for the hydrolysis incubation, and the particular type of protein raw material used. In one embodiment the slurry is incubated with the proteolytic composition at an amount of about 1–10.000 BAPNA proteolytic units/kg of protein-containing raw material, preferably about 10–500 units/kg, including about 25–250 units/kg, such as e.g. about 25–100 units/kg.

In yet another embodiment, at least one non-fish enzyme preparation is added to the fish-derived proteolytic composition prior to the incubation with protein-containing raw material. Such non-fish enzyme preparations include neutral or alkaline proteases such as the commercial protease preparations Neutrase™, Alcalase™ and Flavorzyme™ (from Novo Nordisk, Denmark), Pescalase™ and Fromase™ (both from Gist-Brocades, France), Maxatase™ (Genencor International, Belgium), and Promod 31 ™ (Biocatalysts, UK); lipase preparations such as fungal lipases, e.g. the commercial lipase preparations Palatase™M and Palatase™A (both from Novo Nordisk, Denmark); glycolytic preparations wherein the glycolytic preparation comprises at least one amylase, glucanase, glutaminase, phytase, glycosidase, cellulase, chitinase or pectinase; and any combinations of the above.

In a further useful embodiment of the invention, the aqueous slurry is treated with at least one enzyme preparation such as e.g. one of the above-mentioned preparations, prior to and/or after treatment with the fish-derived proteolytic composition.

The protein-containing material which is hydrolyzed with the method according to the invention is in one embodiment an animal protein selected from the group consisting of a fish protein, shellfish protein, milk protein, whey protein, casein, meat protein, blood protein, egg protein, elastin and gelatin. In another embodiment the protein-containing material is a vegetable protein selected from the group consisting of soy protein; grain protein, e.g. wheat gluten or zein; rapeseed protein; alfalfa protein, pea protein, fabaceous bean protein; cottonseed protein; and sesame seed protein.

In a particularly useful embodiment of the invention, the protein-containing material is marine organism material, such as whole fish, fish flesh, fish viscera, fish skin, fish bones or any part or mixture thereof; or a marine organism material derived from one or more crustacean or a mollusc species including shrimps, lobsters, crayfish, crabs, clams, oysters, and mussels, wherein the material comprises-whole animals, flesh, shells or any parts, mixtures or combinations thereof.

In a yet further useful embodiment, the protein-containing raw material comprises proteinaceous membrane or skin, such as from fish, fish liver, swim bladder of fish, inner body cavity of fish, fish eggs or roe.

Another useful embodiment uses animal-derived protein-containing raw material such as from lamb, pork, beef, chicken, and turkey, wherein the material is either raw or cooked such as by boiling, frying, or curing, and comprises muscle tissue, tendons, other connective tissue, bones, offal or any part or mixture thereof.

It has been found that the method of the invention may be used in combination with a fermentation process, i.e. wherein the protein-containing material is hydrolyzed under fermentation conditions to obtain a fermented protein hydrolysate, and/or wherein the protein hydrolysate obtained by a method according to the invention is subjected to a fermentation process. Examples of such fermentation processes are processes fermenting fish (e.g. in production of fish sauce) cocoa beans or soy (such as in production of soy sauce, tempeh, miso). The addition of the proteolytic enzyme preparation or addition of protein hydrolysate may be useful for decreasing the total process time of the fermentation such as in the curing of herring.

In another aspect, the invention provides protein hydrolysates obtained by the method of the invention. In useful embodiments the protein hydrolysates are derived from animal protein such as any of the above-mentioned. Other embodiments include protein hydrolysates derived from a vegetable protein such as all those previously mentioned.

In a further aspect of the invention, a food product is provided, which product comprises a protein hydrolysate according to the invention. The amount of protein hydrolysate incorporated in the food product will typically be in the range of about 0.1–50% by weight, such as about 0.1–5 wt %.

In a particularly useful embodiment of the invention, the food product is a flavor preparation for use in a food product such as, e.g. a soup, a sauce, a broth, a paté, a mousse, a soufflé, a cheese, frying dough, orly dough, and pastries.

Another food product of the present invention is an ingredient of a mother milk substitute for infants. Due to the high degree of hydrolysis obtained by the method of the invention, the protein hydrolysate of the invention may advantageously be incorporated in mother milk substitutes, the hydrolysate having a significantly lower allergenicity than non-hydrolyzed milk proteins.

Yet another food product of the invention includes the protein hydrolysate of the invention as a protein supplement or to provide other properties of the food product. Thus, the protein hydrolysate incorporated in the food product may for instance be based on fish or fish offal, or meat or scrap meat, rendered from bone by subjecting crushed bone to the method of the invention. Other proteinaceous by-products from the fish industry may also be used by the method of the present invention to generate protein hydrolysates of the invention as a protein supplement or to provide other properties of the food product.

A further aspect of the invention provides a process for preparing a food product, comprising the steps of obtaining a protein hydrolysate according to the invention, and formulating a food product using the hydrolysate. Food products suitably prepared with the process of the invention include all of the above-mentioned.

In another aspect, the invention provides a process of producing a flavor preparation, which process comprises the steps of: preparing an aqueous slurry comprising 1–100 wt % of protein-containing material, such as e.g. about 25 to 100 wt % protein-containing material, depending on the water content and texture of the material; incubating the slurry with a proteolytic composition derived from fish; agitating the slurry for 0,25 to 48 hours, such as in the range of about 1 to 10 hours, preferably about 1.5 to 6 hours, at a temperature in the range of about 2 to about 40° C.; optionally inactivating the proteolytic mixture; separating the solution fraction from solid material; and concentrating the solution to a dry weight content of from about 10 wt % to about 98 wt %.

The optional inactivation step is suitably performed as described above, similarly the agitation step and the concentrating step may be performed with any suitable methods such as those above-mentioned. The fish-derived proteolytic composition is advantageously obtained by any of the methods described above.

In a preferred embodiment, the temperature during the proteolytic incubation is in the range of about 5–30° C., such as in a range of about 10–20° C. or a range of about 10–30° C., including about 15° C. to 25° C. The incubation may be performed at any pH at which the proteolytic composition used is active, in one embodiment the pH during the incubation is in the range of about 6 to 11, preferably from about 6 to about 9.

In a useful embodiment, the invention provides a process for a seafood flavor preparation, wherein the protein-containing material is derived from seafood or seafood byproducts, such as material derived from fish species including cod, haddock, saithe, halibut, flounder, eel, monkfish, salmon, trout, and ocean perch, herring, capelin, and other seafood species including sea urchin, shrimp, lobster, crayfish, crabs, clams, oysters, and mussels.

In a further embodiment, the process according to the invention is for producing a meat flavor preparation, wherein the protein-containing material is derived from meat or meat byproducts. In advantageous embodiments the protein-containing material is derived from one or more species from beef, lamb, pork, reindeer, and poultry species including chicken, turkey, ducks, and ostrich.

In a still further aspect, the invention provides a non-food product comprising a protein hydrolysate according to the invention. The flavor characteristics obtained by the method of the invention are advantageous for production of feed products and pet food.

Furthermore, generation of highly hydrolyzed protein hydrolysates from fish gelatine may improve gelatine products for incorporation into cosmetics, such as creams and shampoos.

The use of the protein hydrolysate of the invention as fermentation medium mentioned above is further makes the hydrolysates of the invention useful for other fermentations as well, such as for a fermentation broth, in particular in the field of medicine for the production of pharmaceutical.

In yet another aspect, the invention provides a method for releasing at least part of the astaxanthin from an astaxanthin-containing shellfish material, the method comprising the steps of preparing as the starting material an aqueous slurry as described comprising the shellfish material; incubating the slurry with a proteolytic composition derived from fish such as described above, agitating the slurry at a temperature in the range of about 2 to 60° C.; and inactivating the proteolytic mixture to obtain a protein hydrolysate containing, relative to the starting material, a higher content of released astaxanthin.

As a further optional step, the method comprises the separation of an astaxanthin-containing aqueous phase, by any suitable means such as sedimentation, filtration, or centrifugation.

The following examples further illustrate the present invention, and they are not intended to be in any way limiting to the scope of the invention as claimed.

EXAMPLE 1

Preparation of a Mixture of Proteases from Cod

About 100 kg of frozen cod viscera, without liver milt and roe were, thawed and added to a four-fold volume of cold potable water in an extraction tank and the pH adjusted to pH 8 to 9 with a sodium hydroxide solution. The mixture was stirred for about 2–6 hours at 0 to 5° C. After a brief period of crude sedimentation (about 30 minutes) the aqueous extract was run off the remaining insoluble viscera with a pump and collected in a sedimentation tank. The aqueous extract was allowed to stand in the cooled sedimentation tank to sediment for about 24 to 60 hours. The supernatant was decanted from the supernatant tank to a holding tank using a pump. The supernatant was concentrated 10 to 20-fold by ultrafiltration and diafiltered to an acceptable level of ionic strength with conductivity below about 3 mS/cm. About 10–15 liters of ultrafiltratered and diafiltered protease preparation was obtained and referred to as Cryotin. The protease preparation had a proteolytic activity of about 1.5 BAPNA units/mL. Repeated preparations using the described procedure gave batch preparations with an activity between about 1 to 5 BAPNA units/mL.

The activity is measured with an assay using the synthetic substrate Benzyl-Arg-p-nitroanilide (BAPNA) at a final substrate concentration of 1 mM in 50 mM Tris-HCl, 10 mM CaCl, pH 8.1, at 25° C. The absorbance increase is measured at 405 nm and the BAPNA activity calculated according to a molar absorbtivity constant of 8800 $M^{-1}cm^{-1}$.

EXAMPLE 2

Purification of Cod Elastase and Cod Serine Collagenases from Concentrated Cod Viscera Extract About 10–15 liters of ultrafiltratered and diafiltered concentrate as obtained in Example 1 was applied to a couple of 1 liter packed chromatography columns connected in a series, the first containing a CM fast flow cation exchange resin (Pharmacia, Sweden), and the second one a DEAE fast flow anion exchange resin (Pharmacia, Sweden) The columns were pre-equilibrated with about 10 column volumes of 25 mM Tris buffer of pH 7.8, containing 2.5 mM calcium chloride (buffer A). The concentrate was pumped onto the columns at a flow rate of about 100 ml per minute. When the application of the concentrated solution onto the columns was completed, residual material was washed off the continuous column system with about 8 L of buffer A. The flow through fraction containing trypsin, chymotrypsin and the exopeptidases is collected and termed Cryotin X.

After this wash was completed, the columns were individually eluted with about 5 column volumes of a high salt solution of 25 mM Tris buffer pH 7.8 containing 0.5 M NaCl and 2.5 mM calcium chloride. The cod elastase was thus desorbed from the CM column and the serine collagenases from the DEAE column.

EXAMPLE 3

Hydrolysis and Release of Protein and Proteinaceous Material from Shrimp Shells using Cryotin Shrimp shells and water were mixed together in the ratio of about 1:0.75 (w/w), by adding 3000 g of shrimp shells to 2250 g of water. An aliquot of 130 ml of Cryotin enzyme mixture of Example 1 containing 1.4 U/ml (BAPNA units), i.e. a total of 182 units per the 3000 g of shrimp shells, or about 0.06 BAPNA hydrolyzing units per gram of shrimp shells. This mixture was reacted by stirring it in a rotating drum for 5 hours at a speed of 40 cycles per minute at room temperature (about 20° C.). The solution fraction was separated from the solid residue by filtration through a course sieve followed by cheesecloth filtration. During the course of the 5-hour reaction-time samples were taken from the reaction mixture for monitoring the reaction. For comparative purposes the reaction was repeated with the same materials except 130 ml of water was added instead of the Cryotin enzyme mixture, and samples were taken for measurements.

With an assay for soluble amino acids and peptides, using TCA (trichloroacetic acid) precipitation followed by reaction with Folin Ciocaletu's reagent, it was revealed that the Cryotin reaction generated more than six fold the amount of soluble amino acids and peptides in five hours compared to the batch with no Cryotin. Furthermore, the Cryotin containing batch generated soluble amino acids and peptides approximately linearly with time throughout the five hour reaction period while the Cryotin-free batch released a burst of soluble amino acids and peptides only in the first hour of the reaction, indicative of the release of already soluble amino acids and peptides but no hydrolysis of protein.

An assay for astaxanthin, employing measurements of absorbance at 468 nm, was used to monitor its release from the shrimp shells. These measurements showed more than a 2.5 fold release of the pigment with the enzymatic Cryotin method than the Cryotin-free method, which probably released pigment primarily with mechanical sheer forces.

EXAMPLE 4

Comparison of Hydrolysis and Solubilization of Protein and Proteinaceous Material from Shrimp Shells Using Cryotin and Alcalase 2.4 L Shrimp shells and water were mixed together in the ratio of 1:0.75 (w/w), by adding 6000 g of shrimp shells to 4500 g of water. An aliquot of 266 ml of Cryotin enzyme preparation of Example 1 containing 110 U/ml (Azocoll units), i.e. a total of 29247 Azocoll units per the 6000 g of shrimp shells, or about 4.87 Azocoll hydrolyzing units per gram of shrimp shells. The mixture was reacted by stirring it in a rotating drum for 5 hours at a speed of 40 cycles per minute at room temperature (about 20° C.). The solution fraction was separated from the solid residue by filtration through a course sieve followed by cheesecloth filtration. During the course of the 5-hour reaction-time samples were taken from the reaction mixture for monitoring the reaction.

For comparative purposes the reaction was repeated with the same materials except now the shrimp shell water mixture was reacted with Alcalase 2.4 L. Shrimp shells and water were mixed together in the ratio of 1:0.75 (w/w), by adding 2500 g of shrimp shells to 1875 g of water. An aliquot of 0.25 ml of the Alcalase 2.4 L enzyme mixture containing 46794.6 U/ml (Azocoll units), i.e. a total of 11699 Azocoll units per the 2500 g of shrimp shells, or about 4.68 Azocoll hydrolysing units per gram of shrimp shells. The mixture was reacted by stirring it in a rotating drum for 5 hours at a speed of 40 cycles per minute at room temperature (about 20° C.). The solution fraction was separated from the solid residue by filtration through a course sieve followed by cheesecloth filtration. During the course of the 5-hour reaction time samples were taken from the reaction mixture for monitoring the reaction.

The Azocoll assay was used to measure comparable activity of Alcalase and Cryotin of Example 1, as Alcalase is known to have very low activity towards BAPNA or GPR. The activity is measured in the following manner: Samples of 50 mg of Azocoll are measured into small glass tubes, 2 samples of Azocoll per each concentration of the enzyme sample to be assayed. Phoshate buffer (100 mM, pH 8.0) was added to each tube to a total final volume of 5 mls. Enzyme samples to be assayed were added to the tubes after the tubes were allowed to stand with only buffer and Azocoll for 5 to 10 minutes. After addition of enzyme samples to the assay mixture the system was allowed to incubate at room temperature for 15 minutes after which the absorbance at 520 nm was measured. The results were first observed as a linear relationship between absorbance at 520 nm vs. amount of enzyme, from which the number of Azocoll hydrolysing units per ml enzyme were calculated, where 1 Azocoll unit (AU) is the amount of enzyme giving rise to an increase in absorbance of 0.1 units.

With an assay for soluble amino acids and peptides, using TCA (trichloroacetic acid) precipitation followed by reaction with Folin Ciocaletu's reagent, it was revealed that the Cryotin reaction generated more than eight-fold the amount of soluble amino acids and peptides in four hours as compared to the batch with Alcalase. An assay for astaxanthin, employing measurements of absorbance at 468 nm, was used to monitor its release from the shrimp shells. These measurements showed more than a 1.6 fold release of the pigment with the enzymatic Cryotin method compared to the Alcalase reaction.

EXAMPLE 5

Production of Food Flavourants from Shrimp Shells Using Cryotin

Shrimp shells (about 20% dry matter) and water were mixed together in a ratio of 1:0.63 (w/w), by adding 3980 g of shrimp shells to 2525 g of water. An aliquot of 165 ml of Cryotin enzyme mixture of Example 1 containing 1.4 U/ml (BAPNA units), i.e. a total of 231 units per the 3980 g of shrimp shells, or about 0.058 BAPNA hydrolyzing units per gram of shrimp shells. This mixture was reacted by stirring it in a rotating drum for 4 hours at a speed of 40 cycles per minute at a temperature of about 15° C. The solution fraction was separated from the solid residue by filtration through a course sieve followed by cheese cloth filtration. The solid residue was used for chitin production. The aqueous fraction was heated to 70° C. for 10 minutes to inactivate the enzymes and pasteurize the fluid. The aqueous phase was then concentrated to 30% dry matter content by evaporation at 45° C. under vacuum.

EXAMPLE 6

Hydrolysis and Release of Proteinaceous Material as Feed from Shrimp Shells Using Cryotin Shrimp shells and water was mixed together in the ratio of 1:0.5 (w/w), by adding 3000 g of shrimp shells to 1500 g of water. An aliquot of 130 ml of Cryotin enzyme mixture of Example 1 containing 1.4 U/ml (BAPNA units), i.e. a total of 182 units per the 3000 g of shrimp shells, or about 0.06 BAPNA hydrolyzing units per gram of shrimp shells. This mixture was reacted by stirring it in a rotating drum for 10 hours at a speed of 40 cycles per minute at a temperature of about 30° C. The solution fraction was separated from the solid residue by filtration through a course sieve followed by cheese cloth filtration. The solid residue was used for chitin production. The aqueous fraction was heated to 70° C. for 10 minutes to inactivate the enzymes and pasteurize the fluid. The aqueous phase was then concentrated to 40% dry matter content by evaporation at 45° C. under vacuum, after which the concentrate was dehydrated further in a drier.

EXAMPLE 7

A Flavor Preparation from Whole Shrimp

Frozen whole shrimp (22.2% dry matter) was minced in a grinder. The ground shrimp and water was mixed together in a ratio of 1:0.75 (w/w), by adding 6700 g of ground shrimp to 5010 g of water. An aliquot of 311 ml of Cryotin enzyme preparation of Example 1 containing 1.4 U/ml (BAPNA units), i.e. a total of 435.4 units to the 6700 g of ground whole shrimp, or about 0.065 BAPNA hydrolyzing units per gram of ground whole shrimp. This mixture was reacted by stirring it in a rotating drum for 4 hours at a speed of 40 cycles per minute at a temperature of about 17° C. The solution fraction was separated from the solid residue by filtration through a course sieve followed by cheese cloth filtration and sedimentation for 10 to 20 minutes. The solid residue was used for chitin production. The aqueous fraction was heated to 70° C. for 10 minutes to inactivate the enzymes and pasteurize the fluid. The aqueous phase was then concentrated to 30 to 40% dry matter content by evaporation at 45° C. under vacuum. The experiment was repeated with the same ratio of raw materials, water and enzyme preparation, except the incubation temperature was kept at 20° C. and the evaporative drying performed at 50° C., resulting in a product of essentially similar quality.

EXAMPLE 8

A Flavor Preparation from Lobster

Lobster heads and claws or whole lobster is used in this preparation, and the raw material is either fresh or frozen. Frozen whole lobster was minced in a grinder. The ground lobster and water was mixed together in a ratio of 1:0.75 (w/w), by adding 8540 g of ground lobster to 6410 g of water. The mixture of lobster and water was brought to 90° C. for a short time (to inactivate, in particular, fenyloxidase present in the lobster) and then cooled down to process temperature which in this example was 35° C. An aliquot of 385 ml of the Cryotin mixture of Example 1 containing 1.4 U/ml (BAPNA units), i.e. a total of 539 units to the 8540 g of ground whole lobster, or about 0.063 BAPNA hydrolysing units per gram of ground whole lobster. This mixture was reacted by stirring it in a rotating drum for 1.5 hours at a speed of 40 cycles per minute at a temperature of about 35° C. The solution extract was separated from the solid residue by filtration through a course sieve followed by cheese cloth filtration and sedimentation for 10 to 20 minutes. The solid residue was used for chitin preparation. The aqueous fraction was heated to 70° C. for 10 minutes to inactivate the enzymes and pasteurize the fluid. The aqueous phase was then concentrated to 40 to 50% dry matter content by evaporation at 45° C. under vacuum.

Subsequent experiments were performed with same ratio of raw materials, water and enzyme preparation, except the pre-heating temperature was 70° C., and the incubation temperature was kept at 30° C., resulting in resulting in a product of essentially similar quality. Same results were achieved with the final concentration step performed at 50° C. to obtain a product of about 30 to 40% dry matter content.

EXAMPLE 9

Flavor Preparation from Pollack

As raw material it is possible to use either the Pollack flesh, i.e. skinned filets of Pollack or Pollack bones, and the raw material may be either fresh or frozen. Fresh skinned Pollack filets were minced in a grinder. The ground Pollack filets and water were mixed together by adding 4750 g of ground Pollack filets with a dry weight content of 21% to 4685 g of water. An aliquot of 292 ml of the Cryotin mixture of Example 1 containing 1.4 U/ml (BAPNA units), i.e. a total of 409 units to the 4750 g of ground Pollack filets or about 0.086 BAPNA hydrolyzing units per gram of ground Pollack filets. This mixture was reacted by stirring it in a rotating drum for 4 hours at a speed of 40 cycles per minute at a temperature of about 26° C. The solution extract fraction was separated from the solid residue by filtration through a course sieve followed by cheesecloth. The aqueous fraction was heated to 70° C. for 10 minutes to inactivate the enzymes and pasteurize the fluid. The aqueous phase was then concentrated to 25 to 35% dry weight content by evaporation at 45° C. under vacuum.

The experiment was repeated with the same ratio of raw materials, water and enzyme preparation, except the incubation temperature was kept at 30° C. and the evaporative drying performed to obtain a product of 18–25% dry weight, resulting in a product of essentially similar quality.

EXAMPLE 10

Preparation of Shrimp Soup Using Flavor Preparation from Whole Shrimp

The following soup recipe is an example of application of the extracts of food flavorants for human consumption. In soup making the extract can ether be used as base material as in the following recipe or as top material, that is added in small amount to almost prepared soup to give it the final taste.

Shrimp Soup for 12 People

Ingredients:

2 onions 2 carrots 2.5 liters water (or fish stock)

2 tablespoons fish bullion 1 tablespoon curry powder 250 g shrimp extract of Example 7

1 garlic clove, chopped 100 g butter, melted+100 g flour 200 mL cream 100 mL white wine The onions and carrots are chopped and stir fried in a saucepan. To the saucepan are added the 2.5 liters water (or fish stock), 2 tablespoons fish bullion, 1 tablespoon curry, 250 g shrimp extract of Example 7,1 garlic clove, chopped. Mixed together and simmered for 20 minutes, then the soup stock is strained. The soup stock is thickened with a mixture of 100 g butter, melted and 100 g flour added to the melted butter. The cream is stirred in the soup and the soup is reheated. Then the white wine is added and whole shrimps for decoration. The soup is ready for serving.

EXAMPLE 11

Removal of Membrane from Squid by Using a Proteolytic Preparation from Cod

Two pieces of frozen whole squid, about 300 g ea., were placed in a rotating drum together with 450 mL water and about 300 mL of Cod-derived proteolytic composition produced as in Example 1, the pH of which had been adjusted to 8.2. The proteolytic composition had an activity of about 105 GPR units/mL, such that total proteolytic activity was about 31400 GPA units, or about 52 GPR units/g of squid (1.7 BAPNA units/g). The pH was adjusted to 8.0 several times during the incubation. The temperature was kept at 10° C. or below, and the squid was inspected and samples taken after 15, 30, 60, 150, 210, and 330 minutes.

The activity is measured with assay using the synthetic substrate Gly-L-Pro-L-Arg-p-nitroanilide (GPR or sGPRpna) at a substrate concentration of 0.3 mM in 50 mM Tris-HCl, 10 mM CaCl, pH 8.1, at 25° C. The absorbance increase is measured at 410 nm and the GPR activity calculated according to a molar absorbtivity constant of 8800 $M^{-1}cm^{-1}$. GPR units are converted to BAPNA units according to the equation $U_{BAPNA}=U_{GPR}/31$.

The following table lists the observations and measurements performed during the course of the experiment.

TABLE 11.1

| time, min. | temp., ° C. | pH | $A_{280}$ | comments |
|---|---|---|---|---|
| 0 | 2 | 8.1 | 0.105 | Squid pieces frozen |
| 15 | 2 | 6.9 | 0.270 | Loosening of membrane observed, one piece becoming slimy on surface, pH adjusted w/NaOH. |
| 30 | 3 | 7.8 | 0.368 | Unchanged from last inspection, pH adjusted w/NaOH. |
| 60 | 4 | 7.6 | 0.510 | Membrane has started to disintegrate. Bladders full of liquid appear on surface. Membrane more slimy. pH adjusted w/NaOH. |
| 150 | 8 | 7.4 | 0.527 | Membrane is loosening shape. pH adjusted w/NaOH. |
| 210 | 10 | 7.6 | 0.580 | Dark part of membrane has almost disappeared from body, still remaining on tail. pH adjusted. |
| 330 | 10 | — | 0.690 | Membrane has almost disappeared from the body and tail. |

It is observed that a proteolytic composition efficiently removes proteinaceous skin and membrane from adhering tissue, such as the membrane on the surface of squid. A corresponding experiment was performed disintegrating the membrane sack of Cod roe.

EXAMPLE 12

Preparation of Hydrolysates from Lamb Meat 107 g fried ground lamb meat was mixed with 163 mL water. The temperature of the slurry was about 25° C. 7 mL of Cryotin with an activity of about 1.4 BAPNA units/mL were mixed with the slurry (i.e. about 0.09 U/g of meat) and the pH adjusted to 7.3 with the addition of NaOH. The slurry was stirred for 4 h. at 20° C. and sample aliquots removed at 1-hour intervals for analysis (pH measurement and absorbance at 280 nm). After completion of the 4 hour incubation, the hydrolysate had a characteristic flavor and aroma of lamb meat. Table 12.1 shows the absorbance measurements for the sampled aliquots, indicating the release of soluble peptides and amino acids.

TABLE 12.1

| time, hours | pH | $A_{280}$ |
|---|---|---|
| 0 | 7.32 | 0.014 |
| 1 | 6.98 | 0.083 |
| 2 | 6.86 | 0.102 |
| 3 | 6.85 | 0.130 |
| 4 | 6.85 | 0.146 |

The experiment was repeated with raw ground lamb meat and similar results were obtained.

EXAMPLE 13

Sensory Testing of Shrimp and Lobster Hydrolysates

A sample of shrimp flavor preparation according to example 7 was subjected to a sensory testing by a test panel consisting of 6 panelists. Before testing, the preparation was diluted by adding 20 g of taste preparation to 200 mL water and heated to about 50° C. The sample was served in small plastic cups. The panelists first evaluated the sample individually by judging the aroma, color, and taste and noted descriptive features and subsequently discussed the general sensory characteristics of the test sample.

Table 13.1 lists comments made by individual panelists.

TABLE 13.1

| color | aroma | taste |
|---|---|---|
| pink (salmon) | sweet, faint aroma, haddock smell | sweet taste, shrimpflesh, haddock, fishflesh |

The panel subsequently reached the following joint conclusion: The shrimp taste preparation had a very characteristic taste and smell of shrimp, esp. a taste of shrimpflesh (also taste of fishflesh).

EXAMPLE 14

Hydrolysis of Protein-Containing Materials with a Refined Proteolytic Composition without Elastase and Serine Collagenases All experiments of Examples 3 to 13 are repeated, except that the Cod-derived proteolytic composition of Example 2 (termed Cryotin X) is used as the hydrolyzing agent. Essentially the same ratio of proteolytic activity, measured as in Example 1, is used, to obtain corresponding results as those described in Examples 3 to 13.

Figure 1:
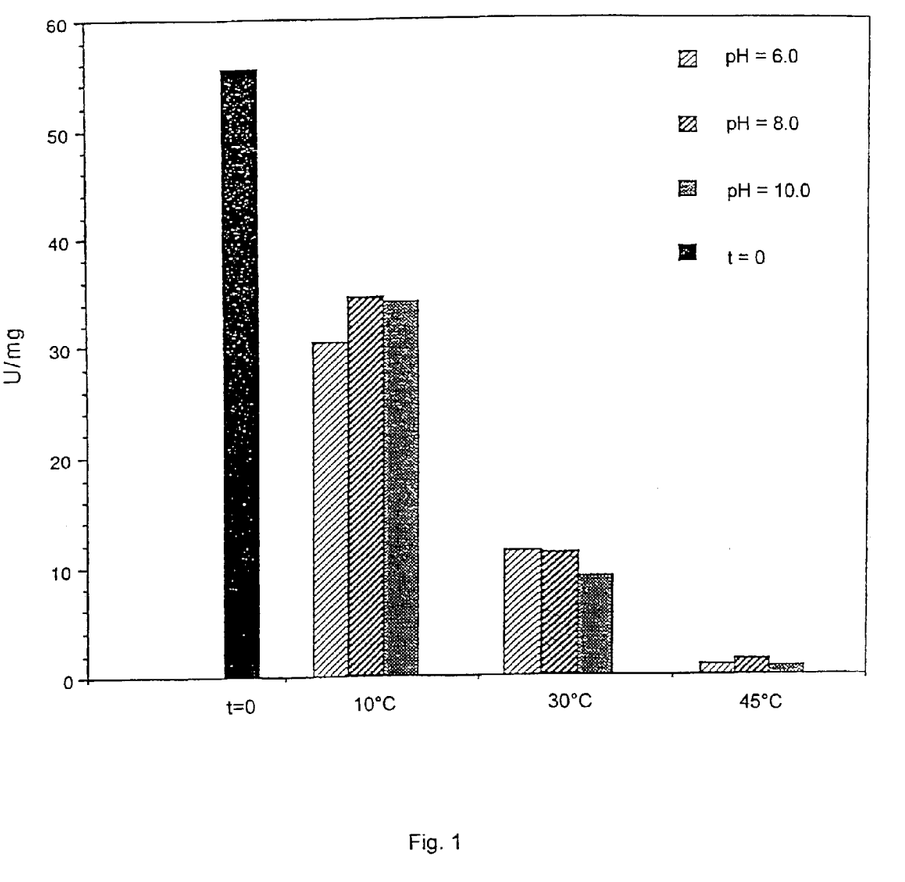

FIG. 1: The stability of the Cod-derived proteolytic composition of Example 1 was measured as a function of temperature and time by observing residual enzyme activity after 24 hour incubations at pH values of 6, 8 and 10 and temperatures of 10°, 30° and 45° C. From this figure one can observe that the proteolytic composition has similar stability characteristics at the three pH values, but is much more stable at low temperatures than high. Enzyme activity was monitored by absorbance measurement at 247 nm at using tosyl arginine methyl ester (TAME). The activity is determined at 25° C. using TAME at a final concentration of 0.075 mM, the assay buffer consists of 40 mM Tris/HCl pH 8.1 and 10 mM $CaCl_2$. One unit of activity is calculated at 1 µmol substrate hydrolyzed/min using a molar extinction coefficient of 540 $M^{-1}cm^{-1}$ at 247 nm.

FIG. 2: The activity of the Cod-derived proteolytic composition of Example 1 is shown as a function of pH using TAME as a substrate. The buffers used at a final concentration of 0.1 M were Hepes/HCl (pH 5.4 to 8.0) and glycinate (pH 8.3 to 10.8) containing 10 mM calcium chloride. From this figure one can observe that the composition has relatively good TAME hydrolyzing activity through the pH range between 7 and 0.10.8, with a maximum between pH about 8.0 and 10.5, where the activity is determined as described in the legend of FIG. 1.

FIG. 3: The temperature dependence of the activity of the Cod-derived proteolytic composition of Example 1. The enzyme activity was monitored using tosyl arginine methyl ester (TAME) as substrate at a final concentration of 0.75 mM. The assay buffer consisted of 40 mM Tris/HCl (pH 8.1) and 10 mM calcium chloride and activity was monitored by following absorbance at 247 nm. From this figure one can observe increasing hydrolytic activity of the composition up to a maximum at around 50° C., after which the activity decreases rapidly due to temperature denaturation. (Activity determined as in legend of FIG. 1.)

The invention claimed is:

1. A method for producing a protein hydrolysate from a natural protein-containing raw material, the method comprising the steps of:
   a) preparing an aqueous slurry comprising 1–100% wet weight of protein-containing material,
   b) incubating the slurry with a proteolytic composition derived from a Gadus species, and
   c) agitating the slurry for 0.25 to 48 hours at a temperature in the range of about 2 to about 40° C.

2. A method according to claim 1, further comprising step d) inactivating the proteolytic mixture.

3. A method according to claim 2, additionally comprising step e) separating the solution fraction from solid material.

4. The method according to claim 1, wherein the proteolytic composition is provided by a process comprising the steps of:
   i) mixing water with fish viscera
   ii) agitating the mixture for a period of 0.5 hours or longer
   iii) separating solid residue from solution
   iv) concentrating the aqueous solution to obtain the proteolytic composition.

5. The method according to claim 4, wherein the agitation is performed at a temperature in the range of about 0 to about 10° C., and at a pH in the range of about 6 to about 9.

6. The method according to claim 1, wherein the proteolytic composition comprises at least one enzyme selected from the group consisting of trypsin, chymotrypsin, elastase, collagenase, aminopeptidase, and a carboxypeptidase type enzyme.

7. The method according to claim 1, wherein the proteolytic composition has a proteolytic activity in the range of about 0.1 to about 50 BAPNA units/mL.

8. The method according to claim 7, wherein the proteolytic composition has a proteolytic activity in the range of about 0.5 to about 10 BAPNA units/mL.

9. The method according to claim 1, wherein the slurry is incubated with the proteolytic composition at an amount of about 10–1000 BAPNA proteolytic units/kg of protein-containing raw material.

10. The method according to claim 9, wherein the slurry is incubated with the proteolytic composition at an amount of about 25–250 BAPNA proteolytic units/kg of protein-containing raw material.

11. The method according to claim 1, wherein the proteolytic composition is further processed by the removal of at least one of its enzyme components.

12. The method according to claim 1, wherein at least one non-fish enzyme preparation is added to the fish-derived proteolytic composition.

13. The method according to claim 1, wherein the aqueous slurry is treated with at least one non-fish enzyme preparation prior to or after treatment with the fish-derived proteolytic composition.

14. The method according to claim 12 or 13, wherein the at least one non-fish enzyme preparation is a lipase preparation.

15. The method according to claim 1, wherein step c) is performed at a temperature in the range of about 5 to about 30° C.

16. The method according to claim 1, wherein step c) is performed at a pH of between about 5 and about 11.

17. The method according to claim 16, wherein step c) is performed at a pH of between about 6 and about 10.

18. The method according to claim 1, wherein the protein-containing material is an animal protein selected from the group consisting of a fish protein, shellfish protein, milk protein, whey protein, casein, meat protein, blood protein, egg protein, elastin and gelatin.

19. The method according to claim 1, wherein the protein-containing material is a vegetable protein selected from the group consisting of soy protein, grain protein, rapeseed protein, alfalfa protein, pea protein, fabaceous bean protein, cottonseed protein, and sesame seed protein.

20. The method according to claim 19, wherein the protein-containing material is a grain protein selected from the group consisting of wheat gluten and zein.

21. The method according to claim 1, wherein the protein-containing material is marine organism material.

22. The method according to claim 21, wherein the marine organism material is a material selected from the group consisting of whole fish, fish flesh, fish offal, fish viscera, fish skin, fish bones and any part or mixture thereof.

23. The method according to claim 21, wherein the protein-containing material is a material including whole animals, flesh, shells or any parts, mixtures or combinations thereof derived from a marine organism selected from the group consisting of crustaceans and molluscs.

24. The method according to claim 23, wherein the crustacean or mollusc is selected from the group consisting of shrimps, lobsters, crayfish, crabs, clams, oysters, and mussels.

25. The method according to claim 1, wherein the protein-containing raw material comprises proteinaceous membrane or skin, swim bladder of fish, inner body cavity of fish, fish eggs or roe.

26. The method according to claim 25, wherein the proteinaceous membrane or skin is derived from fish, fish liver, swim bladder of fish, inner body cavity of fish, fish eggs or roe.

27. The method according to claim 1, wherein the protein-containing raw material comprises lamb, pork, beef, chicken or turkey.

28. The method according to claim 27, wherein the protein-containing material is raw or cooked and comprises muscle tissue, tendons, other connective tissue, bones, offal, and any part or mixture thereof.

29. The method according to any one of the claims 1, 4–9, 11–13, 15, 16, 18, 19, 21–25, 27, 28 comprising as a further step subjecting the protein hydrolysate to a fermentation process.

30. A process of producing a flavor preparation, the process comprising the steps of
   a) preparing an aqueous slurry comprising 1–100% wet weight protein-containing material,
   b) incubating the slurry with a proteolytic composition derived from a *Gadus* species and agitating the slurry for 0.25 to 48 hours at a temperature in the range of about 2 to about 40° C.,
   c) separating solid residue from solution,
   d) concentrating the solution to a dry weight content of from about 10 wt % to about 98 wt %.

31. A process according to claim 30 additionally comprising, after the step b) and before the step c), a step b1) inactivating the proteolytic mixture.

32. The process according to claim 30, wherein the incubation in step b) is performed at a temperature in the range of about 5 to about 30° C.

33. The process according to claim 30, wherein the incubation in step b) is performed at a pH in the range of from about 6 to about 9.

34. The process according to claim 30, wherein the proteolytic composition is obtained by a method comprising the steps of:
  i) mixing water with fish viscera,
  ii) agitating the mixture for a period of 0.5 hours or longer,
  iii) separating solid residue from aqueous solution, and
  iv) concentrating the aqueous solution to obtain the proteolytic composition.

35. The process according to claim 30, wherein the flavor preparation is a seafood flavor preparation, and the protein-containing material is derived from seafood or seafood byproducts.

36. The process according to claim 35, wherein the protein-containing material is derived from one or more species selected from the group containing cod, haddock, saithe, halibut, flounder, eel, monkfish, salmon, trout, ocean perch, herring, capelin, sea urchin, shrimp, lobster, crayfish, crabs, clams, oysters, and mussels.

37. The process according to claim 30, wherein the flavor preparation is a meat flavor preparation, and the protein-containing material is derived from meat or meat byproducts.

38. The process according to claim 37, wherein the protein-containing material is derived from one or more species comprising beef, lamb, pork, reindeer, or poultry species.

39. The process according to claim 38, wherein the protein-containing material is derived from a poultry species selected from the group consisting of chicken, turkey, duck, and ostrich.

40. A method for releasing at least part of the astaxanthin from an astaxanthin-containing shellfish material, the method comprising the steps of preparing as the starting material an aqueous slurry comprising the shellfish material; incubating the slurry with a proteolytic composition derived from a *Gadus* species, agitating the slurry at a temperature in the range of about 2 to 40° C.; and inactivating the proteolytic mixture to obtain a protein hydrolysate containing, relative to the starting material, a higher content of released astaxanthin.

41. A method according to claim 40 comprising as a further step the separation of an astaxanthin-containing aqueous phase.

\* \* \* \* \*